(12) United States Patent
Lele

(10) Patent No.: US 9,777,069 B2
(45) Date of Patent: *Oct. 3, 2017

(54) COMPOSITIONS AND METHODS FOR DETECTION OF METHADONE METABOLITE

(71) Applicant: Siemens Healthcare Diagnostics Inc., Tarrytown, NY (US)

(72) Inventor: Bhalchandra Lele, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 568 days.

This patent is subject to a terminal disclaimer.

(21) Appl. No.: 14/244,992

(22) Filed: Apr. 4, 2014

(65) Prior Publication Data

US 2014/0221626 A1 Aug. 7, 2014

Related U.S. Application Data

(62) Division of application No. 13/364,718, filed on Feb. 2, 2012, now Pat. No. 8,771,964.

(51) Int. Cl.
*C07K 16/40* (2006.01)
*C07K 16/44* (2006.01)
*G01N 33/53* (2006.01)
*G01N 33/94* (2006.01)

(52) U.S. Cl.
CPC ............. *C07K 16/40* (2013.01); *C07K 16/44* (2013.01); *G01N 33/9486* (2013.01)

(58) Field of Classification Search
CPC ..... C07K 16/40; C07K 16/44; G01N 33/9486
See application file for complete search history.

(56) References Cited

U.S. PATENT DOCUMENTS

| 5,073,629 A | 12/1991 | Dubler et al. |
| 5,518,887 A | 5/1996 | Parsons et al. |
| 5,710,256 A | 1/1998 | Buechler |
| 6,140,137 A | 10/2000 | Sigler et al. |
| 8,771,964 B2 * | 7/2014 | Lele ............ G01N 33/9486 435/188 |
| 2005/0048666 A1 | 3/2005 | Larson et al. |
| 2006/0046273 A1 | 3/2006 | Lin et al. |
| 2007/0129434 A1 | 6/2007 | Smith-Carliss et al. |

FOREIGN PATENT DOCUMENTS

| EP | 0380019 A2 | 8/1990 |
| WO | 9631496 A1 | 10/1996 |
| WO | 9854133 A1 | 12/1998 |
| WO | 2007128133 A1 | 11/2007 |

OTHER PUBLICATIONS

Richard A. Goldsby, "Immunology," Macmillan, Nov. 29, 2002, p. 69.*
Wolf et al., "Evaluation of an Enzyme Immunoassay for the Detection of Methadone Metabolite EDDP [2-Ethylidene-1,5-Dimethyl-3,3-Diphenylpyrrolidine] in Urine", Journal of Clinical Laboratory Analysis, Jan. 6, 2014, vol. 28, Issue 2, pp. 136-140.
Supplementary Partial European Search Report of European Patent Application No. EP 13743365 dated Jun. 8, 2015.
Depriest et al. "Urine Drug Testing of Chronic Pain Patients. III. Normetabolites as Biomarkers of Synthetic Opioid Use" Journal of Analytical Toxicology, vol. 34, Oct. 2010. entire document.
International Search Report and Written Opinion of International Application No. PCT/US2013/023051 dated Mar. 29, 2013.
European Search Report and Search Opinion of European Patent Application No. EP 13743365.2 dated Sep. 28, 2015.

* cited by examiner

*Primary Examiner* — Galina Yakovleva
(74) *Attorney, Agent, or Firm* — Cynthia G. Tymeson

(57) ABSTRACT

Methods and reagents are disclosed for conducting assays for EDDP. The reagents include a moiety selected from the group consisting of poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties linked to 2-ethylidene-1, 5-dimethyl-3,3-diphenylpyrrolidine at the 3-position of one of the phenyl rings. Antibodies produced from immunogenic EDDP conjugates and labeled EDDP conjugates are employed in assays for determining the presence and/or amount of EDDP in samples suspected of containing EDDP.

3 Claims, 7 Drawing Sheets

COMPOSITIONS AND METHODS FOR DETECTION OF METHADONE METABOLITE

This application is a Continuation of U.S. Ser. No. 13/364,718 filed Feb. 2, 2012, issued as U.S. Pat. No. 8,771,964 on Aug. 8, 2014.

BACKGROUND

This invention relates to compounds, methods and kits for the determination of methadone metabolites in samples, such as patient samples, known or suspected to contain such methadone metabolites.

Methadone is used in pain management and in the treatment of opiate addiction, either from naturally-occurring opioids or synthetically produced opioids such as, e.g., heroin. It is necessary to monitor compliance with methadone treatment in order to prevent illegal use of the prescribed medicine. Monitoring methadone concentration is not very reliable as significant portion of patient population has high rate of methadone metabolization, which can result in an incorrect determination regarding the issue of compliance. In addition, non-compliant patients can add methadone to their samples, which can wrongly indicate compliance. Methadone is metabolized primarily into a pharmacologically inactive metabolite 2-ethylidene-1,5-dimethyl-3,3-diphenylpyrrolidine (EDDP) although other metabolites are also formed.

There is a continuing for assays to accurately determine one or both of a presence and an amount of a methadone metabolite in samples suspected of containing the same.

SUMMARY

Some examples in accordance with the principles described herein are directed to a compound comprising a moiety selected from the group consisting of poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties linked to 2-ethylidene-1,5-dimethyl-3,3-diphenylpyrrolidine at the 3-position of one of the phenyl rings.

Some examples in accordance with the principles described herein are directed to a compound of the Formula I:

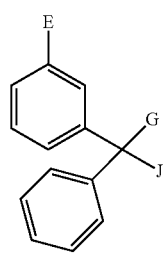

Formula I wherein:
E is L-Q wherein L is a bond or a linking group and Q is H, alkyl, a protecting group, C(O)OH, CF$_3$C(O)OH, a halogen, a poly(amino)acid, a non-poly(amino)acid, a maleimido group, a bromoacetamido group, an acrylate, a methacrylate ester, an amide, an amine, a thiol, a hydroxyl, an aldehyde, or a nitrile, for example;

G is cyano, carboxyl, carboxyl ester, ketone, or amide, for example;
J is H or

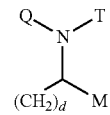

wherein M is H, alkyl, aryl or acyl, for example; Q is H, alkyl, aryl or acyl, for example; T is H, alkyl, C(O)O(CH$_2$)$_m$CCl$_3$, C(O)O(CH$_2$)$_m$CBr$_3$, aryl or acyl, for example; and wherein d is an integer of 1 to about 5 and m is an integer of 1 to 5; or
J and H may be taken together to form a spiro linked pyrrolidine ring.

Some examples in accordance with the principles described herein are directed to a compound of the Formula II:

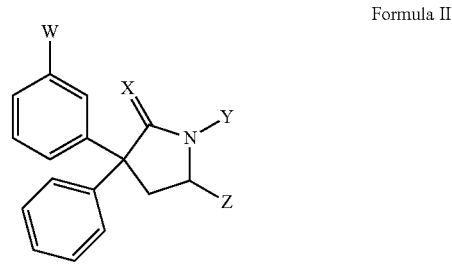

Formula II wherein:
X is NH, N-alkyl, oxygen, sulfur, S-alkyl, imine or ketone, for example;
Y is alkyl, aryl or acyl, for example;
Z is H, alkyl, aryl or acyl, for example; and
W is selected from the group consisting of OH, O(CH$_2$)$_f$CH$_3$, O-protecting group, O(CH$_2$)$_g$COOH, O(CH$_2$)$_h$C(O)NH(CH$_2$)$_j$)NHC(O)—O-protecting group, O(CH$_2$)$_k$C(O)NH(C$_2$)$_n$NHCF$_3$COOH, O(CH$_2$)$_p$C(O)NH(CH$_2$)$_q$NHC(O)(CH$_2$)$_r$-moiety, a maleimido group, a bromoacetamido group, an acrylate, a methacrylate ester, an amide, an amine, a thiol, a hydroxyl, an aldehyde, or a nitrile, for example, wherein f, g, h, j, k, n, p, q and r are each independently an integer of 1 to about 5.

Some examples in accordance with the principles described herein are directed to assay methods utilizing the aforementioned compounds for the detection of 2-ethylidene-1,5-dimethyl-3,3-diphenylpyrrolidine in a sample suspected of containing 2-ethylidene-1,5-dimethyl-3,3-diphenylpyrrolidine.

DETAILED DESCRIPTION OF SPECIFIC EMBODIMENTS

EDDP Conjugates

Figure 1:
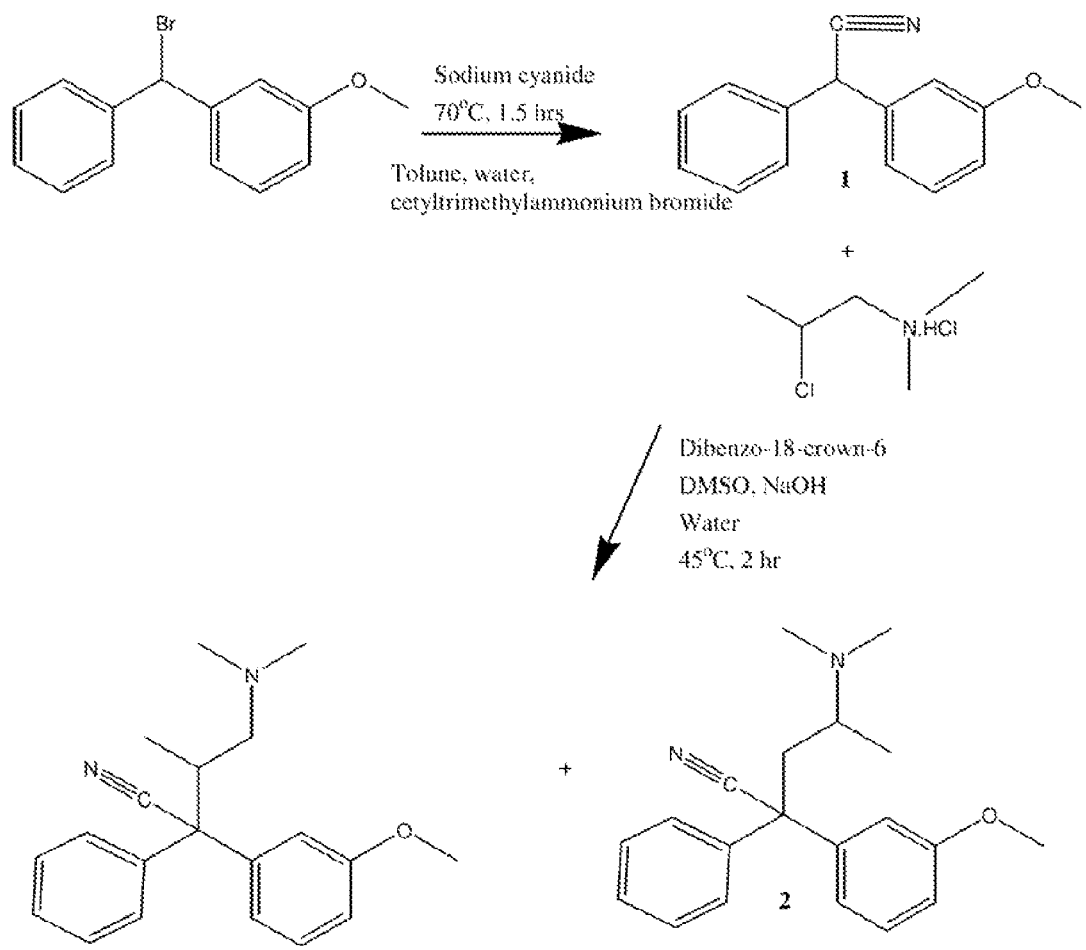
FIG. 1 is a depiction of an example of a reaction scheme for preparing compounds in accordance with the principles described herein.

The present inventors have discovered that compounds wherein a moiety is linked to 2-ethylidene-1,5-dimethyl-3,3-diphenylpyrrolidine (EDDP) at a meta-position (3-position) of a phenyl ring of EDDP are useful as immunogens for generating antibodies for EDDP and as labeled entities for use in assays for EDDP. As a result EDDP may be monitored with an accurate and sensitive assay as part of determining a subject's compliance with methadone therapy.

Some examples in accordance with the principles described herein are directed to a compound comprising a moiety, selected from the group consisting of poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties linked to 2-ethylidene-1,5-dimethyl-3,3-diphenylpyrrolidine at the 3-position of one of the phenyl rings. When the moiety is an immunogenic carrier, the compounds may be employed to raise antibodies for EDDP. When the moiety is a label moiety, the compounds may be employed as label entities in assays for the detection of EDDP.

The term "poly(amino acid) label moieties" includes labels that are proteins such as, but not limited to, enzymes, antibodies, peptides, and immunogens, for example. With label proteins such as, for example, enzymes, the molecular weight range will be from about 10,000 to about 600,000, or from about 10,000 to about 300,000 molecular weight. There is usually at least about 1 EDDP analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of EDDP analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

The term "non-poly(amino acid) labels" includes those labels that are not proteins. The non-poly(amino acid) label is capable of being detected directly or is detectable through a specific binding reaction that produces a detectable signal. The non-poly(amino acid) label can be isotopic or non-isotopic and can be, by way of illustration and not limitation, a radioisotope, a luminescent compound, a polynucleotide coding for a catalyst, a promoter, a dye, a coenzyme, an enzyme substrate, a radioactive group, a small organic molecule (including, e.g., biotin, fluorescent molecules, and chemiluminescent molecules), an amplifiable polynucleotide sequence, a support such as, for example, a plate, a particle (including bead) such as latex or carbon particle or chromium dioxide (chrome) particle or the like, metal sol, crystallite, liposome, cell, etc., which may or may not be further labeled with a dye, catalyst or other detectable group, for example.

A poly(amino acid) label or a non-poly(amino acid) label may be it member of a signal producing system. The signal producing system may have one or more components, at least one component being the label, whether poly(amino acid) or non-poly(amino acid). The signal producing system generates a signal that relates to the presence of a sirolimus compound in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic, radiation, desirably by visual examination. Exemplary signal-producing systems are described in U.S. Pat. No. 5,508,178 (Rose, et al.), the relevant disclosure of which is incorporated herein by reference.

Immunogenic carriers include certain poly(amino acids) and non-poly(amino acids). By the term "immunogenic carrier" is meant a group which, when conjugated to a hapten and injected into a mammal, will induce an immune response and elicit the production of antibodies that bind to the hapten. Haptens are compounds capable of binding specifically to corresponding antibodies, but do not themselves act as immunogens (or antigens) ter preparation of the antibodies. Antibodies that recognize a hapten can be prepared against compounds comprised of the hapten linked to an immunogenic (or antigenic) carrier. Immunogenic carriers may also be referred to as antigenic carriers. Typical immunogenic carriers include, without limitation, poly (amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference.

The molecular weight range for poly(amino acids) that are immunogenic carriers such as protein antigens is from about 5,000 to about 10,000,000, or from about 20,000 to about 600,000, or from about 25,000 to about 250,000 molecular weight. Poly(amino acid) immunogenic carriers include, but are not limited to, proteins such as, for example, albumins, serum proteins, e.g., globulins, ocular lens proteins and lipoproteins, for example. Illustrative proteins include, by way of illustration and not limitation, bovine serum albumin (BSA), keyhole limpet hemocyanin ("KLH"), egg ovalbumin, and bovine gamma-globulin (BGG), for example. Non-poly(amino acid) immunogenic carriers include, but are not limited to polysaccharides, particles, poly(lysines), and polyethylene glycols), for example.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

The term "support" includes any organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, DENDRIMERS, and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), for example; either used by themselves or in conjunction with other materials. Other supports include, but are not limited to, polysaccharides, particularly cross-linked polysaccharides, such as agarose, dextran, cellulose, and starch, for example.

A linking group as described herein may be employed to bind the EDDP analog in accordance with the principles described herein to a solid support, provided only that the linking group does not substantially interfere with the EDDP analog's ability to bind with an antibody. In some examples, the binding of the EDDP analog may be the result of coating or covalently binding directly to the solid support or to one or more layers of one or more carrier molecules such as poly(amino acids) including proteins such as serum albumins or immunoglobulins, or polysaccharides (carbohydrates) such as, for example, dextran or dextran derivatives. Other methods of binding the EDDP analog are also possible. For instance, a solid support may have a coating of a binder for a small molecule such as, for example, avidin or an antibody, and a small molecule such as e.g., biotin or a hapten, can be bound to the EDDP analog or vice versa.

When the support is a particle, the average diameter of the particle is at least about 0.02 microns and not more than about 100 microns. In some examples, the particles have an average diameter from about 0.05 microns to about 20 microns, or from about 0.3 microns to about 10 microns, for example. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic, phospholipid vesicles, chylomicrons, lipoproteins, and the like. In some examples, the particles are chrome particles or latex particles.

The terms "non-label poly(amino acid) moieties" and "non-immunogenic carrier poly(amino acid) moieties" mean poly(amino acids) that are not normally considered labels or immunogenic, carriers although such moieties may be labels or immunogenic carriers in certain circumstances. For example, an antibody may not be considered a label but may be a label if the antibody is modified to include a signal producing moiety or part of a signal producing system. Furthermore, an antibody may not be considered as an immunogenic carrier but is nonetheless capable of being an immunogenic carrier in certain circumstances because of it higher molecular weight.

The moiety is linked to the meta-position of a phenyl ring of EDDP directly by a bond or indirectly through a linking group. In some examples, the linking group has a molecular weight less than about 2000, or less than about 1500, or less than about 1000, or less than about 500, or less than about 300, or less than about 200, or less than about 150, for example. Such linking groups may comprise about 2 to about 200 atoms, or 4 to about 150 atoms, or about 5 to about 100 atoms, or about 5 to about 50 atoms, or about 5 to about 25 atoms, not counting hydrogen, and may comprise a chain of from 2 to about 100 atoms, or 3 to about 90 atoms, or about 4 to about 80 atoms, or about 5 to about 70 atoms, or about 10 to about 50 atoms, or about 10 to about 25 atoms, or about 5 to about 20 atoms, or about 5 to about 10 atoms, for example, each independently selected from the group consisting of carbon, oxygen, sulfur, nitrogen, and phosphorous. The number of heteroatoms in such linking groups is dependent on the size of the linking group and, in some examples, the number is in the range of from 0 to about 30, or 1 to about 25, or about 2 to about 20, or about 2 to about 15, or about 2 to about 10, or about 3 to about 10, or about 3 to about 5, for example. The heteroatoms may be in the form of one or more functionalities, such as, for example, ether, ester, urea, carbamate, sulfonamide, thioether, hydrazone, hydrazide, amidine, and phosphate ester. In one example in accordance with the principles described herein, the linking group comprises two nitrogen atoms and two carbonyl groups in a chain of about 8 to about 20 atoms including carbon atoms.

For the most part, when a linking group has a linking functionality (functionality for reaction with a moiety) such as, for example, a non-oxycarbonyl group including nitrogen and sulfur analogs, a phosphate group, an amino group, alkylating agent such as halo or tosylalkyl, oxy (hydroxyl or the sulfur analog, mercapto) oxycarbonyl (e.g., aldehyde or ketone), or active olefin such as a vinyl sulfone or α-, β-unsaturated ester, these functionalities are linked, to amine groups, carboxyl groups, active olefins, alkylating agents, e.g., bromoacetyl. Where art amine and carboxylic acid or its nitrogen derivative or phosphoric, acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. For other examples of linking groups see, for example, Cautrecasas, *J. Biol. Chem.* (1970) 245:3059.

Some examples in accordance with the principles described herein include compounds of the Formula I:

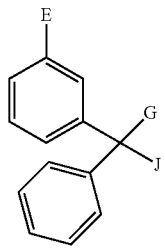

Formula I wherein:
E is L-Q wherein L is a bond or a linking group as described herein and Q is H; alkyl; a protecting group; C(O)OH; $CF_3C(O)OH$; a halogen (bromine, chlorine, fluorine and iodine); a poly(amino)acid, a non-poly(amino)acid, a halogen, a poly(amino)acid, a maleimido group, a bromoacetamido group, an acrylate, a methacrylate ester, an amide, an amine, a thiol, a hydroxyl, an aldehyde, or a nitrile, for example;
G is cyano, carboxyl, carboxyl ester, ketone, or amide, for example;
J is H or

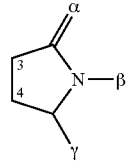

M is H, alkyl, aryl or acyl, for example; Q is H, alkyl, aryl or acyl, for example; T is H, alkyl, $C(O)O(CH_2)_mCCl_3$, $C(O)O(CH_2)_mCBr_3$, aryl or acyl, for example; and wherein d is an integer of 1 to 5, or 1 to 4, or 1 to 3, or 1 to 2, or 2 to 5, or 2 to 4, or 2 to 3, or 3 to 5, or 3 to 4, or 4 to 5, for example, and m is an integer of 1 to 5, or 1 to 4, or 1 to 3, or 1 to 2, or 2 to 5, or 2 to 4, or 2 to 3, or 3 to 5, or 3 to 4, or 4 to 5, for example; or J and H may be taken together to form a spiro linked pyrrolidine ring.

The term "alkyl" refers to a branched or unbranched saturated monovalent hydrocarbon radical containing 1 to 10, or 1 to 5, or 1 to 4, or 1 to 3, or 1 to 2, or 2 to 5, or 2 to 4, or 2 to 3, or 3 to 5, or 3 to 4, or 4 to 5 carbon atoms. Alkyl includes, but is not limited to, methyl, ethyl, propyl, butyl and pentyl, and including the normal, secondary, and tertiary, forms thereof where appropriate. The alkyl groups may be substituted or unsubstituted. "Substituted" means that a hydrogen atom of a molecule is replaced by another atom, which may be a single atom such as a halogen, or heteroatom, or part of a group of atoms forming, for example, alkyl groups, heteroatom substituted alkyl groups, cyclic structures or heterocyclic structures. The term "aryl" means an organic radical derived from an aromatic hydrocarbon by the removal of one atom and containing one or more aromatic rings, usually one to four aromatic rings, such as, e.g., phenyl (from benzene), naphthyl (from naphthalene), etc., e.g., phenyl, naphthyl, phenanthryl. The term "acyl" means RC(O)— where R is alkyl or aryl.

Suitable protecting, groups include, by way of example and not limitation, t-butyldimethylsilyl, t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyl-oxycarbonyl, alpha-dimethyl-3,5-dimethoxybenxyloxycarbonyl, o-nitrophenylsulfenyl, 2-cyano-1,1-dimentylethoxycarbonyl, bromobenzyloxy, and carbamyl, formyl, for example. See also, for example, "Principles of Peptide Synthesis" (M. Bodanszky. Springer Verlag, Berlin, Heidelberg, New York, Tokyo (1984 for a listing of protecting groups.

In some examples in accordance with the principles described herein, the pyrrolidine ring of the compound of Formula I has the formula:

wherein:
α is NH, N-alkyl, oxygen, S, or S-alkyl, for example;
β is H, alkyl, aryl or acyl, for example;
γ is H, alkyl, an or acyl, for example; and
the pyrrolidine ring is spiro linked, through position 3, for example; and
E is $—O-Q^1$ or $—NHQ^1$ or $—SQ^1$ wherein $Q^1$ is H; alkyl; a protecting group; $(CH_2)_a$-T wherein T is C(O)OH, C(O)NH $(CH_2)_b$NH—V wherein V is $CF_3C(O)OH$, —C(O)—O-protecting group, $C(O)(CH_2)_cR$ wherein R is a halogen, maleimido group, bromoacetamido group, acrylate, methacrylate ester, amide, amine, thiol, hydroxyl, aldehyde, nitrile, a poly(amino acid) label moiety, a non-poly(amino acid) label moiety, a poly(amino acid) immunogenic carrier, a non-poly(amino acid) immunogenic carrier, a non-label poly(amino acid) moiety, or a non-immunogenic carrier poly(amino acid), for example, and wherein a is an integer of 1 to 5, or 1 to 4, or 1 to 3, or 1 to 2, or 2 to 5, or 2 to 4, or 2 to 3, or 3 to 5, or 3 to 4, or 4 to 5, for example, b is an integer of 1 to 5, or 1 to 4, or 1 to 3, or 1 to 2, or 2 to 5, or 2 to 4, or 2 to 3, or 3 to 5, or 3 to 4, or 4 to 5, for example, and c is an integer of 1 to 5, or 1 to 4, or 1 to 3, or 1 to 2, or 2 to 5, or 2 to 4, or 2 to 3, or 3 to 5, or 3 to 4, or 4 to 5, for example.

Some examples in accordance with the principles described herein include compounds of the formula:

Formula II wherein:
X is NH, N-alkyl, oxygen, sulfur, S-alkyl, imine or ketone, for example;
Y is H, alkyl, aryl or acyl, for example;
Z is H, alkyl, aryl or acyl, for example; and
W is selected from the group consisting of OH, $O(CH_2)_f$ $CH_3$, O-protecting group, $O(C_2)_gCOOH$, $O(CH_2)_hC(O)NH$ $(CH_2)_j$NHC(O)—O-protecting group, O(CH$_2$)$_k$C(O)NH(CH$_2$)$_n$NHCF$_3$COOH, O(CH$_2$)$_p$C(O)NH (CH$_2$)$_q$NHC(O)(CH$_2$)$_r$-moiety, a maleimido group, a bromoacetamido group, an acrylate, a methacrylate ester, an amide, an amine, a thiol, a hydroxyl, an aldehyde, or a nitrile, for example, wherein f, g, h, j, k, n, p, q and r are each independently an integer of 1 to 5, or 1 to 4, or 1 to 3, or 1 to 2, or 2 to 5, or 2 to 4, or 2 to 3, or 3 to 5, or 3 to 4, or 4 to 5, for example.

Preparation of EDDP Conjugates

Figure 2:
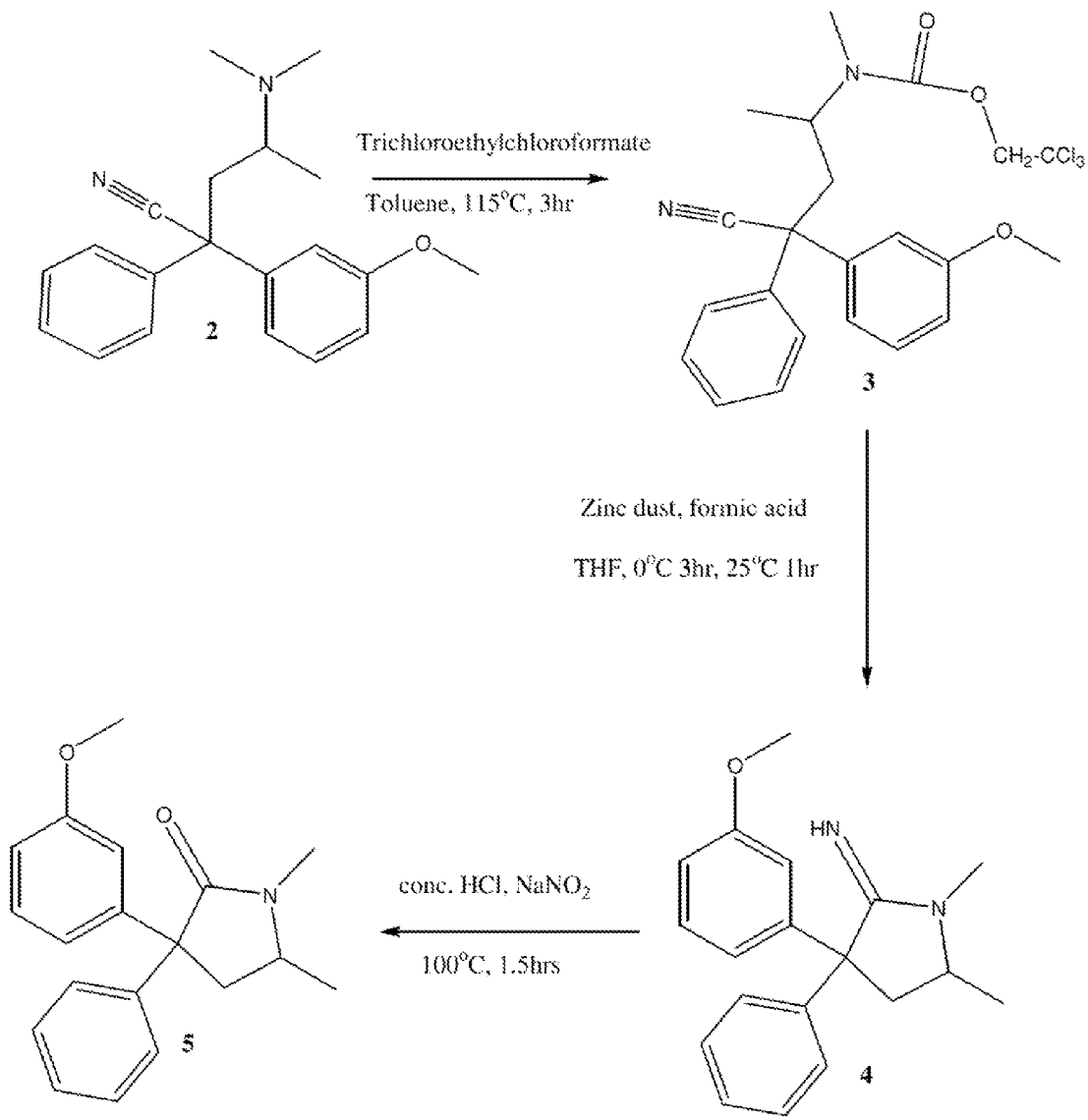
FIG. 2 is a depiction of an example of a reaction scheme for preparing compounds in accordance with the principles described herein.
Figure 3:
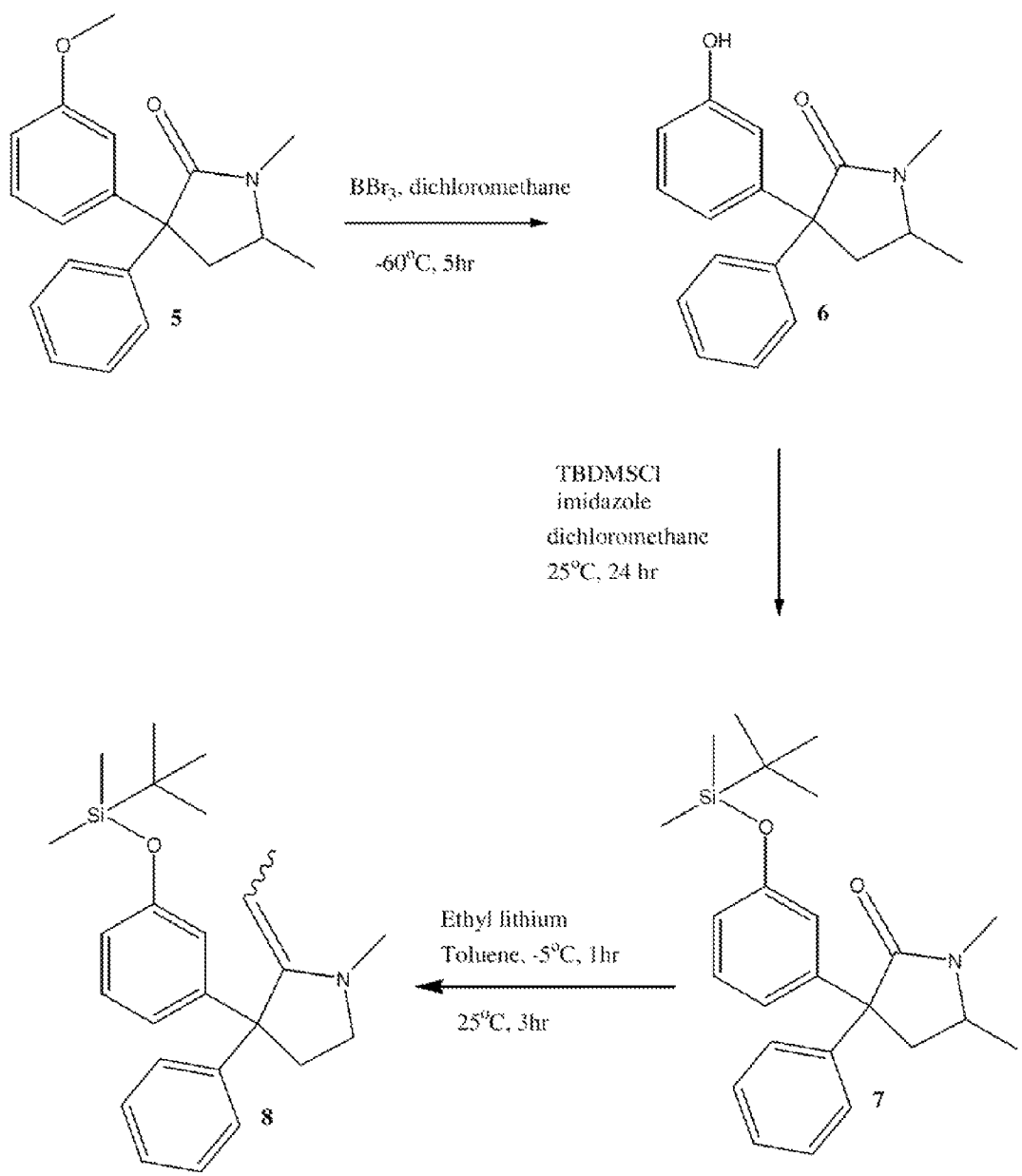
FIG. 3 is a depiction of an example of a reaction scheme for preparing compounds in accordance with the principles described herein.
Figure 4:
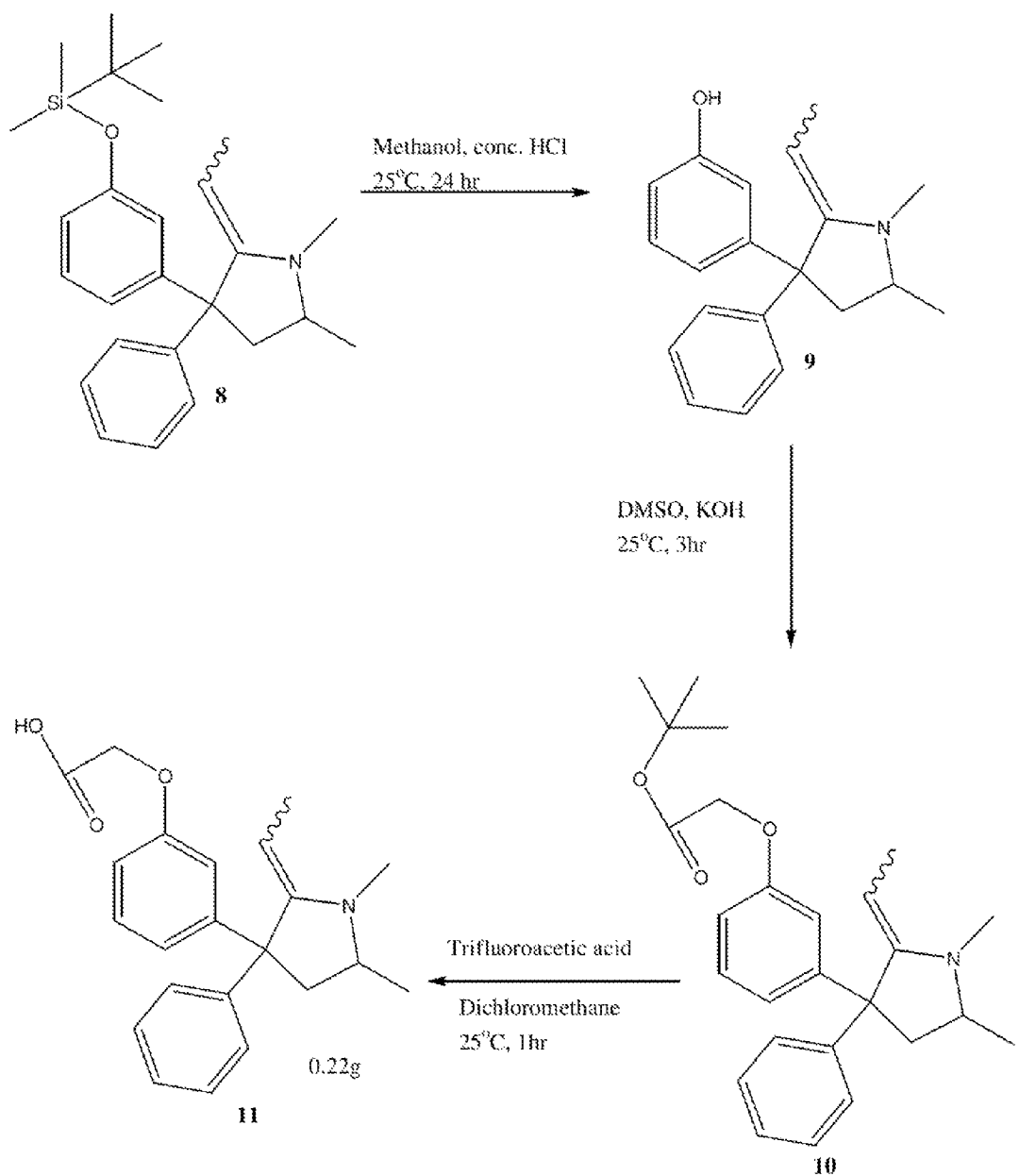
FIG. 4 is a depiction of an example of a reaction scheme for preparing compounds in accordance with the principles described herein.
Figure 5:
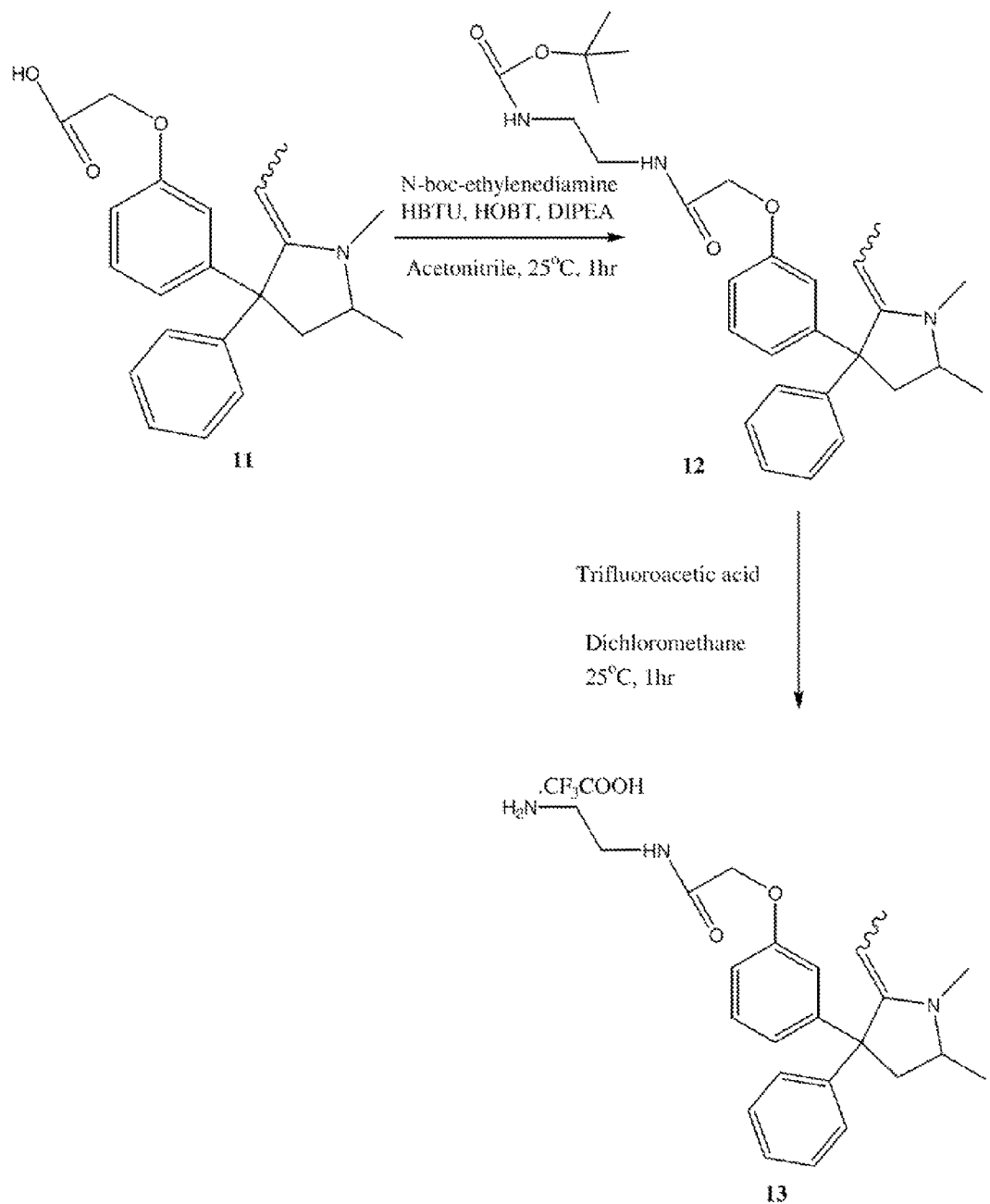
FIG. 5 is a depiction of an example of a reaction scheme for preparing compounds in accordance with the principles described herein.
Figure 6:
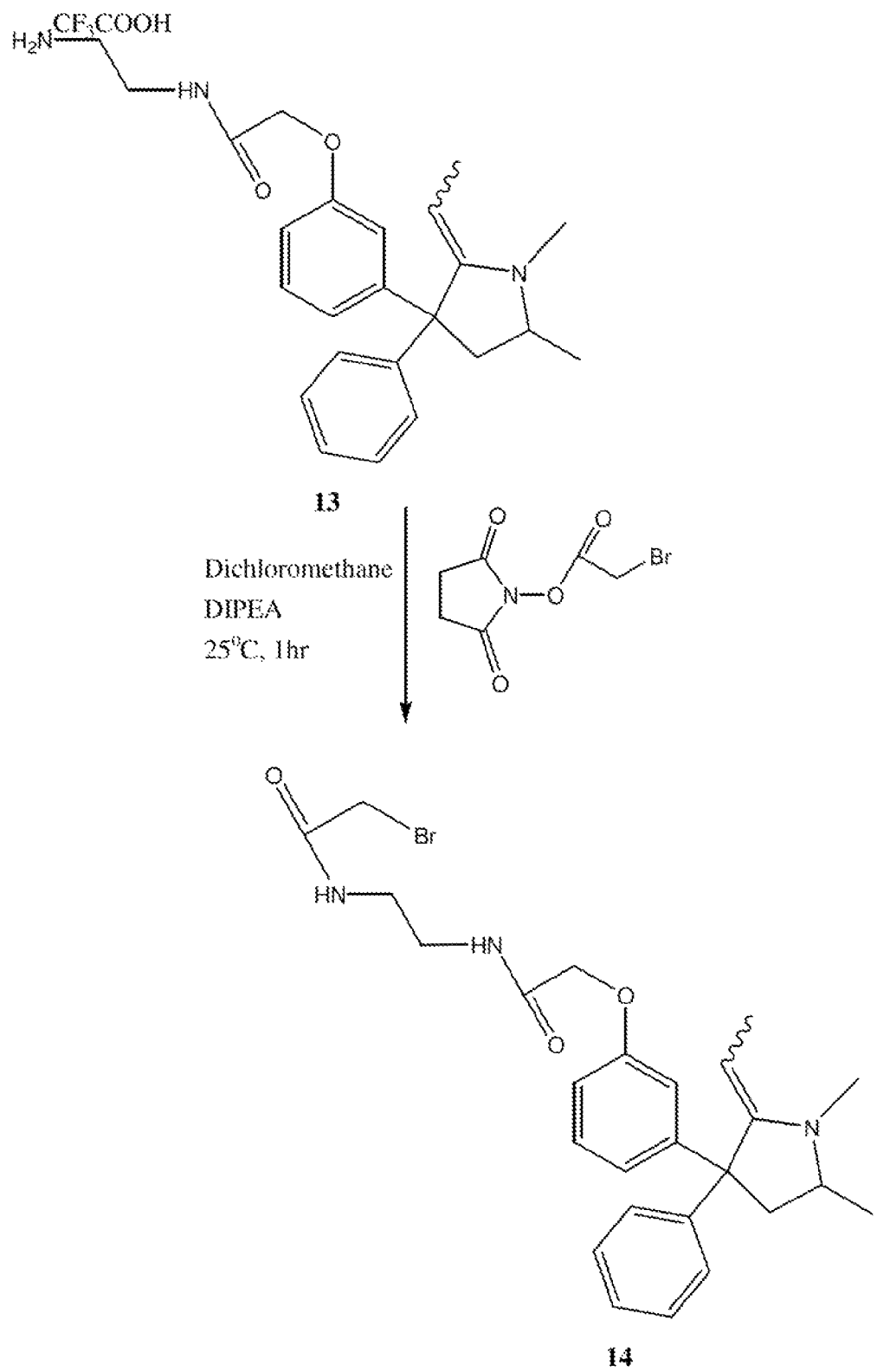
FIG. 6 is a depiction of an example of a reaction scheme for preparing compounds in accordance with the principles described herein.
Figure 7:
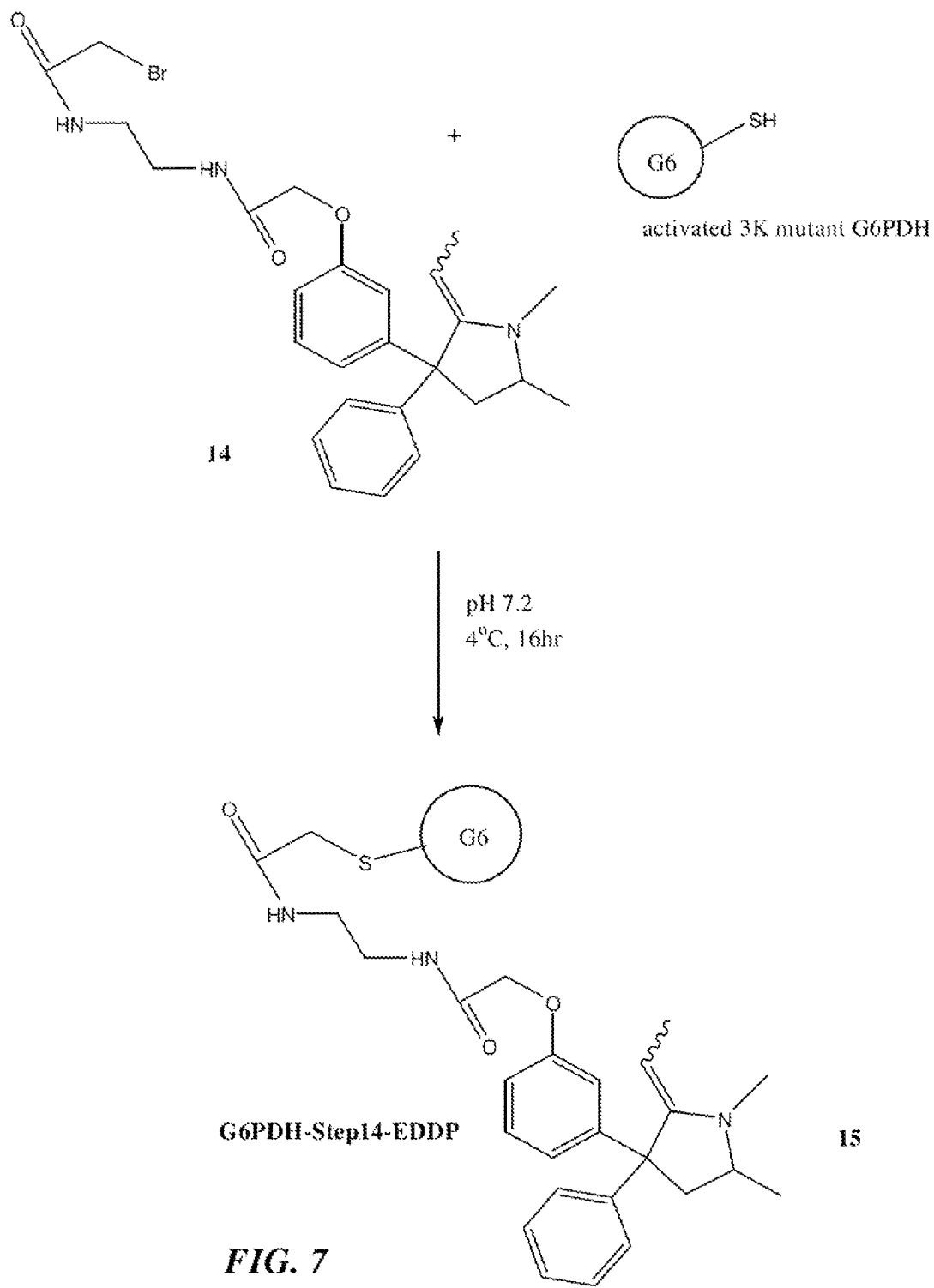
FIG. 7 is a depiction of an example of a reaction scheme for preparing compounds in accordance with the principles described herein.

Examples of syntheses of meta-substituted EDDP derivatives are described with reference to FIGS. 1-7 by way of illustration and not limitation. The compound 2-(3-methoxyphenyl)-2-phenylacetonitrile (1) is synthesized by reacting 3-methoxybenzhydryl bromide with a cyanide metal salt such as, for example, sodium cyanide or potassium cyanide, in the presence of a phase transfer catalyst such as, for example, cetyltrimethylammonium bromide, cetyltrimethylammonium chloride, or tetrabutylammonium bromide. The reaction is carried out in an aqueous medium containing about 5 to about 50% (by volume) of an aromatic solvent such as, for example, toluene, xylene or benzene. The temperature during the reaction is about 40 to about 115° C., or about 70° C., for a period of about 1 hour to about 6 hours, or about 1.5 hours.

An alkyl chain containing an N-methyl group is inserted into 1 by nucleophilic substitution with 2-dimethylaminoisopropyl chloride under very mild reaction conditions in the presence of a crown ether as a catalyst, which results in a 20% increase in the percentage of desired isomer (4-dimethylamino)-2-3-(methoxyphenyl)-2-phenylacetonitrile (2). The reaction is carried out in an aqueous medium containing about 5 to about 50% (by volume) of a polar organic solvent such as, for example, dimethylsulfoxide (DMSO), dimethylformamide (DMF) or dimethylacetamide. The temperature during the reaction is about 25 to about 75° C. or about 45° C., and the reaction is conducted for a period of about 1 hour to about 6 hours, or about 2 hours.

N-demethylation of 2 is performed by reaction of 2 with trichloroethylchloroformate to obtain 2,2,2-trichloroethyl 4-cyano-4-(3-methoxyphenyl)-4-phenylbutan-2-yl(methyl) carbamate (3). The reaction is carried out in an aromatic organic solvent such as, for example, toluene, xylene or benzene. The temperature during the reaction is about 70 to about 130° C., or about 115° C., and the duration of the reaction is about 1 hour to about 6 hours, or about 3 hours.

Zinc-formic acid catalyzed intramolecular cyclization of 3 gives 3-(3-methoxyphenyl)-1,5-dimethyl-3-phenylpyrrolidin-2-imine (4) with a five member ring required for recognition of EDDP in an immunoassay. The reaction is carried out in a polar organic solvent such as, for example, an ether (e.g., tetrahydrofuran (THF), dimethylformamide, dimethylsulfoxide, and dimethylacetamide acetone. The temperature during the reaction is about −5 to about 25° C., or about 0° C., for a period of about 1 hour to about 16 hours, or about 3 hours, and at a temperature of about 0 to about 35° C., or about 25° C., for a period of about 0.5 hour to about 16 hours, or about 1 hour.

The imine group in 4 is hydrolyzed by in situ generation of nitrous acid to obtain 3-(3-methoxyphenyl)-1,5-dimethyl-3-phenylpyrrolidin-2-one (5). The reaction is carried out in a concentrated mineral acid such as, for example, hydrochloric acid, sulfuric acid, or nitrous acid, in the presence of a nitrite metal salt such as, for example, sodium nitrite or potassium nitrite. The temperature during the reaction is about 0 to about 120° C., or about 100° C., and the reaction is conducted for a period of about 1 hour to about 6 hours, or about 1.5 hours.

The methoxy group in the meta-position of 5 is de-protected by reaction of 5 with boron tribromide to obtain 3-(3-hydroxyphenyl)-1,5-dimethyl-3-phenylpyrrolidin-2-one (6). The reaction is carried out in the presence of a metal halogenide as a demethylation agent such as, for example, boron tribromide or boron trichloride. The solvent for the reaction is an organic solvent such as, for example, dichloromethane, chloroform, or THF. The temperature during the reaction is about −80 to about 25° C., or about −60° C., and the reaction is conducted for a period of about 1 hour to about 16 hours, or about 6 hours.

The free phenolic —OH group in 6 is re-protected by a protecting group such as, for example, t-butyldimethylsilyl, trimethylsilyl, or benzyl group to obtain 3-(3-(t-butyldimethylsilyloxy)phenyl)-1,5-dimethyl-3-phenylpyrrolidin-2-one (7). The reaction is carried out in the presence of a t-butyldimethylsilyl halide such as, for example, chloride or bromide. The solvent for the reaction is an organic solvent such as, for example, dichloromethane, chloroform, THF, or acetone. The temperature during the reaction is about 0 to about 70° C., or about 25° C., and the reaction is conducted for a period of about 1 hour to about 48 hours, or about 24 hours.

The carbonyl group in 7 is convened to an ethylidene group by reaction of 7 with an alkyl (1 to 5 carbon atoms) lithium such as, for example, ethyl lithium, propyl lithium or butyl lithium, to obtain 3-(3-(t-butyldimethylsilyloxy)phenyl)-2-ethylidene-1,5-dimethyl-3-phenylpyrrolidine (8). The reaction is carried out in an aromatic organic solvent such as, for example, toluene, xylene or benzene. The reaction is conducted at a temperature of about −15 to about 25° C., or about −5° C., for a period of about 0.5 hour to about 6 hours, or about 1 hour, and then at a temperature of about 15 to about 60° C., or about 25° C., for a period of about 1 hour to about 6 hours, or about 3 hours.

The phenolic —OH group is de-protected by mild acid hydrolysis to obtain 3-(2-ethylidene-1,5-dimethyl-3-phenylpyrrolidin-3-yl)phenol (9). The hydrolysis reaction is carried out using a concentrated mineral acid such as, for example, hydrochloric acid, sulfuric acid or nitric acid, in a polar organic solvent such as, for example, an alcohol (e.g., methanol, ethanol). The reaction is conducted at a temperature of about 0 to about 100° C., or about 25° C., for a period of about 1 hour to about 48 hours, or about 24 hours.

T-butyl bromoacetate is reacted with the free phenolic —OH group of 9 to obtain t-butyl 2-(3-(2-ethylidene-1,5-dimethyl-3-phenylpyrrolidin-3-yl)phenoxy)acetate (10). The reaction is carried out in the presence of an alkali metal hydroxide such as, for example, potassium hydroxide, sodium hydroxide, or lithium hydroxide, in a polar organic solvent such as, for example, DMSO, DMF, or dimethylacetamide. The reaction is conducted at a temperature of about 15 to about 60° C. or about 25° C. for a period of about 1 hour to about 24 hours, or about 3 hours.

Acid hydrolysis of 10 removes the t-butyl group to give 2-(3-(2-ethylidene-1,5-dimethyl-3-phenylpyrrolidin-3-yl)phenoxy)acetic acid (11) with free carboxyl group. The reaction is carried out in the presence of a strong, organic acid such as, for example, trifluoroacetic acid or trichloroacetic acid, in an organic solvent such as, for example, dichloromethane, chloroform or THF. The reaction is conducted at a temperature of about 0 to about 60° C. or about 25° C., for a period of about 0.5 hour to about 24 hours, or about 1 hour.

N-boc-ethylenediamine is reacted with the carboxyl group in 11 to obtain t-butyl 2-(2-(3-(2-ethylidene-1,5-dimethyl-3-phenylpyrrolidin-3-yl)phenoxy)acetamido)ethylcarbamate (12). The reaction is carried out in the presence of one or more peptide coupling agents such as, for example, O-Benzotriazole-N,N,N',N'-tetramethyl-uronium-hexafluoro-phosphate (HBTU), 1-hydroxybenzotriazole (HOBT), O—(N-succinimidyl)-1,1,3,3-tetramethyluronium tetrafluoroborate (TSTU), 2-(1H-1-7-azabenzotriazol-1-yl)-1,1,3,3-tetramethyl uranium hexafluorophosphate (HATU), benzotriazol-1-yl-oxytripyrrolidinophosphonium hexafluorophosphate (PyBOP) and O-(benzotriazol-1-yl)-N,N,N',N'-tetramethyluronium tetrafluoroborate (TBTU), and N,N-diisopropylethylamine (DIPEA) and mixtures thereof in a polar organic solvent such as, for example, acetonitrile, THF, DMF, or DMSO. The reaction is conducted at a temperature of about 0 to about 60° C., or about 25° C., for a period of about 0.5 hour to about 24 hours, or about 1 hour.

The N-hoc group in 12 was removed by reaction of 12 with trifluoroacetic acid to obtain N-(2-aminoethyl)-2-(3-(2-ethylidene-1,5-dimethyl-3-phenylpyrrolidin-3-yl)phenoxy) acetamide 2,2,2-trifluoroacetate (13) with a free amine group. The reaction is carried out in the presence of a strong organic acid such as, for example, trifluoroacetic acid or trichloroacetic acid, in an organic solvent such as, for example, dichloromethane, THF or chloroform. The reaction is conducted at a temperature of about 15 to about 60° C., or about 25° C., for a period of about 0.5 hour to about 24 hours, or about 1 hour.

The removal of protecting groups in the above synthesis is dependent on the nature of the protecting group, for example. The deprotection agent may be acidic agent such as, for example, trifluoroacetic acid and water, or a basic agent such as, for example, piperidine and DMF. Conditions such as solvents, temperature, pH, and duration of treatment, for example, are dependent on the nature of the protecting group, for example.

The amine group in 13 is converted to a thiol-reactive bromoacetamido group to obtain 2-bromo-N-(2-(2-(3-(2-ethylidene-1,5-dimethyl-3-phenylpyrrolidin-3-yl)phenoxy) acetamido)ethyl)acetamide (14) by reaction of 13 with N-hydroxysuccinimidyl ester of 2-bromoacetic acid. The reaction is carried out in the presence of a base such as, for example, DIPEA or triethylamine, in an organic solvent such as, for example, dichloromethane, chloroform or THF. The reaction is conducted at a temperature of about 15 to about 60° C., or about 25° C., for a period of about 0.5 hour to about 24 hours, or about 1 hour.

An example, by way of illustration and not limitation, of a conjugation of compound 14 with a moiety is represented by the synthesis of G6PDH-14 EDDP conjugate (15). Glucose-6-phosphate dehydrogenase (3K mutant G6PDH with two cysteine residues per enzyme) is reacted with 14 to obtain G6PDH-14 EDDP conjugate as follows. Activated G6PDH is dissolved in an aqueous buffer such as, for example, phosphate buffer, acetate buffer or borate buffer, containing a chelating agent such as, for example, ethylenediaminetetraacetate (EDTA), in the presence of a reducing agent such as, for example, dithiothreitol, cysteine or mercaptoethanol, at a pH of about 6 to 8, or about 7.2. To this solution is added thiol-reactive 14 dissolved in a polar organic solvent such as, for example, DMF, DMSO, or dimethylacetamide. The reaction is conducted at a temperature of about 0 to about 25° C., or about 4° C., for a period of about 1 hour to about 36 hours, or about 24 hours. The G6PDH-14 EDDP conjugate is purified by chromatography such as, for example, gel filtration chromatography or high performance liquid chromatography (HPLC).

Preparation of Antibodies with Immunogenic EDDP Conjugates

Conjugates of 14 with poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties may be synthesized in a manner similar to that described above for the G6PDH-14 EDDP conjugate.

Examples of immunogenic carrier EDDP conjugates in accordance with the principles described herein may be employed to prepare antibodies specific for EDDP. By the phrase "antibody or antibodies specific for EDDP" is meant an antibody that binds specifically to EDDP and does not bind to any significant degree to other entities such that the analysis for EDDP would be distorted.

Antibodies specific for EDDP for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete or intact immunoglobulin or fragments thereof, which immunoglobulins include the various classes and isotypes, such as IgA, IgD, IgE, IgG1, IgG2a, IgG2b and IgG3, IgM, etc. Fragments thereof may include Fab, Fv, and F(ab')$_2$, Fab', and the like. When the IgG is digested enzymatically, different fragments are obtained depending on the enzyme used; for instance, if papain is used, three fragments are obtained, the carbohydrate-containing fragment (Fc) and two antigen-binding fragments (Fab) and, if pepsin is used, one F(ab')$_2$ fragment is obtained, while the carbohydrate-containing fragment is digested. The foregoing is due to the fact that papain cuts the heavy chains immediately after the hinge region (towards the amino terminal region), while pepsin cuts them before the hinge (towards the carboxy terminal region). When treated with a reagent capable of reducing disulfide bonds, the F(ab')$_2$ fragment is broken into two fragments, called Fab' that have the same immunological properties as the Fab fragments produced by papain digestion. In addition to intact antibody and antibody fragments, aggregates, polymers, and conjugates of immunoglobulins or of their fragments can be used where appropriate so long as binding affinity for a particular molecule is maintained.

Antiserum containing antibodies (polyclonal) is obtained by well-established techniques involving immunization of an animal, such as a rabbit, sheep, horse, chicken, guinea pig, goat, or the like with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1-24 (1975); Broughton and Strong, Clin. Chem. 22: 726-732 (1976); and Mayfair, et al., Br. Med. Bull. 30:24-31 (1974).

Antibodies can also be obtained by somatic cell hybridization techniques, such antibodies being commonly referred to as monoclonal antibodies. Monoclonal antibodies may be produced according to the standard techniques of Köler and Milstein, *Nature* 265:495-497, 1975. Reviews of monoclonal antibody techniques are found in Lymphocyte Hybridomas, ed. Melchers, et al. Springer-Verlag (New York 1978), Nature 266:495 (1977), Science 208: 692 (1980), and Methods of Enzymology 73 (Part B): 3-46 (1981). In another approach for the preparation of antibodies, the sequence coding for antibody binding, sites can be excised from the chromosome DNA and inserted into a cloning vector, which can be expressed in bacteria to produce recombinant proteins having the corresponding antibody binding sites.

General Description of Assays for EDDP Utilizing the Present Compounds

Examples of antibodies specific for EDDP prepared from immunogenic EDDP conjugates in accordance with the principles described herein may be employed in assays for the determination of EDDP in a sample. Examples of label conjugates in accordance with the principles described herein may be employed as a label reagent in assays for the determination of EDDP in a sample.

An assay can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling, assays, for example, where an antibody raised against an immunogen in accordance with the principles described herein comprises a label and/or a label conjugate in accordance with the principles described herein is employed in the assay.

One general group of immunoassays includes immunoassays using a limited concentration of the present conjugate reagent. Another group of immunoassays involves the use of an excess of one or more of the principal reagents such as, for example, an excess of the present conjugate reagent. Another group of immunoassays are separation-free homogeneous assays in which a labeled reagent in accordance with the principles described herein modulates the label signal upon binding of the present conjugate to EDDP in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et. al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow et al., J. Clin Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA") the enzyme membrane immunoassays ("EMIA"); luminoimmunoassays ("LIA"); and so forth. Other types of assays include immunosensor assays involving the monitoring of the changes in the optical, acoustic and electrical properties of the present conjugate upon the binding of EDDP analyte. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for EDDP bound thereto is contacted with a medium containing the sample suspected of containing EDDP and a labeled EDDP conjugate in accordance with the principles described herein. EDDP in the sample competes with the EDDP conjugate bearing the detectable label for binding to the EDDP antibody. After separating the support and the medium, the label activity of the support or the medium is determined by conventional techniques and is related to the amount of EDDP analyte in the sample.

The support may be comprised of an organic or inorganic, solid or fluid, water insoluble material, which may be transparent or partially transparent. The support can have any of a number of shapes, such as a particle (particulate support) including bead, a film, a membrane, a tube, a well, a strip, a rod, and planar surfaces such as, e.g., plate, paper, etc., fiber, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

In some assay examples the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

In some examples, a sample to be analyzed is combined in an assay medium with an antibody for EDDP and labeled EDDP. The antibody may be an antibody raised against an immunogenic conjugate in accordance with the principles described herein or raised against another EDDP conjugate. The labeled EDDP may be a label conjugate in accordance with the principles described herein or another labeled EDDP conjugate. The medium is examined for one or both of the presence and amount of a complex comprising EDDP and the antibody for EDDP where the presence and/or the amount of such complex indicates the presence and/or amount of EDDP in the sample.

The sample to be analyzed is one that is suspected of containing EDDP. The samples are preferably from a mammalian subject, e.g., humans or other animal species and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum.

The sample can be prepared in any convenient medium. Conveniently, the sample may be prepared in an assay medium, which is discussed more fully hereinbelow. In some instances a pretreatment may be applied to the sample such as, for example, to lyse blood cells. In some examples, such pretreatment is performed in a medium that does not interfere subsequently with an assay.

The assays are normally carried out in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as albumins; organic solvents such as formamide; quaternary ammonium salts; polyanions such as dextran sulfate; binding enhancers, e.g., polyalkylene glycols; polysaccharides such as dextran, trehalose, or the like. The medium may also comprise agents for preventing the formation of blood clots. Such agents are well known in the art and include, for example, EDTA, EGTA, citrate, heparin, and the like. The medium may also comprise one or more preservatives as are known in the art such as, for example, sodium azide, neomycin sulfate, PROCLIN® 300, Streptomycin, and the like. Any of the above materials, if employed, is present in a concentration or amount sufficient to achieve the desired effect or function.

As mentioned above, the sample and the antibody reagent and the labeled EDDP reagent are combined in the assay medium. Depending on the nature of the assay employed, the medium or one or both of the above reagents may comprise one or more components such as, for example, a solid support (e.g., a particle) and other members of a signal producing system of which the label is a part, for example.

One or more incubation periods may be applied to the medium at one or more intervals including any intervals between additions of various reagents employed in an assay including those mentioned above. The medium is usually incubated at a temperature and for a time sufficient for binding of various components of the reagents and binding of EDDP in the sample to occur. Moderate temperatures are normally employed for carrying out the method and usually constant temperature, preferably, room temperature, during the period of the measurement. In some examples, incubation temperatures range from about 5 to about 99° C., or from about 15° C. to about 70° C., or about 20° C. to about 45° C. The time period for the incubation, in some examples, is about 0.2 seconds to about 24 hours, or about 1 second to about 6 hours, or about 2 seconds to about 1 hour, or about 1 minute to about 15 minutes. The time period depends on the temperature of the medium and the rate of binding of the various reagents, which is determined by the association rate constant, the concentration, the binding constant and dissociation rate constant.

In an example of a method for determining EDDP in a sample suspected of containing EDDP, a combination is provided in a medium where the combination includes the sample, an antibody for EDDP, and a labeled EDDP compound in accordance with the principles described herein where the label is a poly(amino acid) label or a non-poly (amino acid) label. The antibody for EDDP may be an antibody raised against an immunogen conjugate of EDDP in accordance with the principles described herein. However, for this example, the antibody can be any antibody specific for EDDP. The medium is examined for one or both of the presence and amount of a complex comprising EDDP and the antibody for EDDP. The presence and/or the amount of the complex indicates the presence and/or amount of EDDP in the sample.

In another example of a method for determining EDDP in a sample suspected of containing EDDP, the sample suspected of containing EDDP is combined in a medium with an antibody raised against an immunogen conjugate of EDDP in accordance with the principles described herein and with a label conjugate of be an antibody raised against an immunogen conjugate of EDDP in accordance with the principles described herein. The label conjugate of EDDP may be in accordance with the principles described herein or the label conjugate may be any labeled conjugate of EDDP. The medium is examined for the presence and/or amount of a complex comprising EDDP and the antibody and the presence and/or amount of the complex indicates the presence of EDDP in the sample.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light, which results in activation of another member of the sps.

In some embodiments of known assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member. i.e., the amount of sps member bound or not bound to the EDDP analyte being detected or to an agent that reflects the amount of the EDDP analyte to be detected. In some examples in accordance with the principles described herein, one of either the sensitizer reagent or the chemiluminescent reagent comprises the present conjugate reagent. Examples of photosensitizers and chemiluminescent reagents that may be utilized are those set forth in U.S. Pat. Nos. 5,340,716 and 6,251,581, the relevant disclosures of which are incorporated herein by reference.

In a particular example, an induced luminescence immunoassay may be employed. The induced luminescence immunoassay is referred to in U.S. Pat. No. 5,340,716 (Ullman), which disclosure is incorporated, herein by reference. In one approach, the assay uses a particle having associated therewith a photosensitizer where an EDDP conjugate in accordance with the principles described herein is bound to the particle. The chemiluminescent reagent comprises an antibody for EDDP. The EDDP analyte competes with the particle-bound EDDP for the antibody for EDDP. If the EDDP analyte is present, the fewer is the number of molecules of photosensitizer-EDDP conjugate that come into close proximity with the chemiluminescent compound. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of EDDP analyte present in the sample.

In one example of the induced luminescence assay, a photosensitizer particle is employed that is conjugated to avidin or streptavidin. A conjugate of EDDP and biotin is also employed where the conjugate is in accordance with the principles described, herein. A chemiluminescent reagent that comprises a binding partner for EDDP is employed as part of the detection system. The reaction medium is incubated to allow the avidin or streptavidin of the photosensitizer particles to bind to the biotin-EDDP conjugate by virtue of the binding between avidin and biotin and to also allow the binding partner for the EDDP analyte that is part of the chemiluminescent reagent to bind to the EDDP analyte or to the EDDP conjugate on the photosensitizer particles. Then, the medium is irradiated with light to excite the photosensitizer, which is capable in its excited state of activating oxygen to a singlet state. Because less of the chemiluminescent reagent is now in close proximity to the photosensitizer because of the presence of the EDDP analyte, there is less activation of the chemiluminescent reagent by the singlet oxygen and emits luminescence. The medium is then examined for the presence and/or the amount of luminescence or light emitted, the presence thereof being related to the presence and/or amount of the EDDP analyte where a decrease in signal is observed in the presence of the EDDP analyte.

The concentration of the EDDP analyte that may be assayed generally varies from about $10^{-5}$ to about $10^{-17}$ M, more usually from about $10^{-6}$ to about $10^{-14}$ M. Considerations, such as whether the assay is qualitative, semiquantitative or quantitative (relative to the amount of the EDDP analyte present in the sample), the particular detection technique and the expected concentration of the EDDP analyte normally determine the concentrations of the various reagents.

The concentrations of the various reagents in the assay medium will generally be determined by the concentration range of interest of the EDDP analyte, the nature of the assay, and the like. However, the final concentration of each of the reagents is normally determined empirically to optimize the sensitivity of the assay over the range of interest. That is, a variation in concentration of EDDP analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Examination Step

In a next step of an assay method, the medium is examined for the presence of a complex comprising the EDDP analyte and antibody for EDDP. The presence and/or amount of the complex indicates the presence and/or amount of the EDDP analyte in the sample.

The phrase "measuring the amount of an EDDP analyte" refers to the quantitative, semiquantitative and qualitative determination of EDDP. Methods that are quantitative, semiquantitative and qualitative, as well as all other methods for determining the EDDP analyte, are considered to be methods of measuring the amount of the EDDP analyte. For example, a method, which merely detects the presence or absence of the EDDP analyte in a sample suspected of containing the EDDP analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the EDDP analyte in the sample. The particular mode of detection depends on the nature of the sps. As discussed above, there are numerous methods by which a label of an sps can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C. In one approach standard curves are formed using known concentrations of the EDDP analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of EDDP analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conduction Assays

Labeled EDDP conjugates in accordance with the principles described herein or antibodies for EDDP raised against immunogenic EDDP conjugates in accordance with the principles described herein and other reagents for conducting a particular assay for EDDP analyte may be present in a kit useful for conveniently performing an assay for the determination of an EDDP analyte. In some embodiments a kit comprises in packaged combination a biotin-binding partner such as, for example, avidin or streptavidin, associated with a particle, biotinylated EDDP conjugate in accordance with the principles described herein and an enzyme labeled antibody for the EDDP analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, sps members, ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a conjugate of EDDP in accordance with the principles described herein. The kit can further include a written description of a method utilizing reagents that include a conjugate in accordance with the principles described herein.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designations "first" and "second" are used solely for the purpose of differentiating between two items such as, for example, "first sps member" and "second sps member," and are not meant to imply any sequence or order or importance to one item over another.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

Examples

Unless otherwise indicated, materials in the experiments below may be purchased from the Sigma-Aldrich Chemical Corporation, St. Louis Mo. The amino acid derivatives for peptide synthesis may be purchased from EMD Chemicals, Gibbstown N.J., Biotin-dPEG4-NHS ester may be purchased from Quanta Biodesign, Powell Ohio. Parts and percentages disclosed herein are by weight unless otherwise indicated.

Definitions hr=hour(s)
rpm=revolutions per minute
mg=milligram
g=gram(s)
mL=milliliter(s)
° C.=degrees Centigrade
min=minute(s)
conc=concentrated
NHS=N-hydroxysuccinimide
DTT=dithiothreitol
kDa=kilodalton(s)
mAu=milli absorbance unit.

Preparation of Meta-Substituted EDDP Compounds

Step 1: 2-(3-methoxyphenyl)-2-phenylacetonitrile 3-methoxybenzhydrol (200 g) was dissolved in toluene (2000 mL). To this solution was added anhydrous calcium bromide (200 g). Hydrogen bromide gas was bubbled through the reaction mixture for 2 hr at 25° C. with stirring. The reaction mixture was filtered and transferred into another flask and argon gas was purged through the flask for 1 hr. Cetyltrimethylammonium bromide (6 g) was added to the toluene solution of 3-methoxybenzhydryl bromide prepared as above. The toluene solution was heated to 70° C. and sodium cyanide (50 g) dissolved in water (500 mL) and preheated to 70° C. was added to the solution. The reaction mixture was stirred at 70° C. for 1.5 hr at 800 rpm. Then the reaction mixture was cooled to 25° C. and was extracted with ethyl acetate (2000 mL). The organic layer was dried on anhydrous sodium sulfate, filtered and evaporated wider vacuum at 37° C. A dark brown viscous liquid (160 g) was obtained as crude product.

Purification of the crude product was carried out on a BIOTAGE® AB ISOLERA™ (Charlotte N.C.) flash chromatography system as follows: Crude product (80 g) was dissolved in ethyl acetate (80 mL) and loaded onto the chromatography system's SNAP cartridge containing 1500 g silica gel. The product was eluted with a step gradient of ethyl acetate and hexane. Fractions containing the product were pooled and evaporated under vacuum to obtain a viscous yellow liquid. Yield of purified product (combined runs): 40 g. 1H NMR (CDCl3): 3.7 δ (3H, —OCH3), 5.1 δ (1H, —CH—CN), 6.8-7.5 δ (9H, phenyl rings), Mass spectrometry: m/z=141 (M+H2O)

Step 2: 4-(dimethylamino)-2-(3-methoxyphenyl)-2-phenylpentanenitrile

The product of Step 1 (60 g) was dissolved in dimethylsulfoxide (60 mL). To this, dibenzo-18-crown-6 (2.25 g) was added followed by addition of a solution of sodium hydroxide (45 g) dissolved in water (50 mL), which was cooled to room temperature. The reaction mixture was stirred at 25° C. To this, 2-dimethylaminoisopropyl hydrochloride was added in small portions. The addition was complete in 10 min and the reaction mixture temperature rose to 45° C. The flask containing reaction mixture was then immersed in an oil bath preheated to 45° C. The stirring was continued at 45° C. for 2 hr. Then, the reaction mixture was diluted with chloroform (2000 mL) and extracted twice with 500 mL water each. The organic layer was dried on anhydrous magnesium sulfate, filtered and concentrated to obtain a viscous yellow liquid containing regioisomers of the product.

The desired isomer of Step 2 was separated on the BIOTAGE® AB ISOLERA™ flash chromatography system as follows: The crude product (15 g) was loaded on a SNAP cartridge containing 340 g silica gel. The column was eluted with a gradient of acetone and hexane. The desired isomer of step 2 eluted last. Yield of purified product (combined runs): 38 g. 1H NMR (CDCl3): 0.9 δ (3H, —CH—CH3 of isopropyl), 2.1 δ (6H, —N—(CH3)2), 2.3 δ (1H, —CH—CH3 of isopropyl), 2.6 and 2.8 δ (1H, 1H, —CH2-CH—CH3 of isopropyl), 3.8 δ (3H, —OCH3), 6.8-7.5 δ (9H, phenyl rings). Mass spectrometry: m/z=309 (M+H)

Step 3: 2,2,2-trichloroethyl 4-cyano-4-(3-methoxyphenyl)-4-phenylbutan-2-yl(methyl)carbamate The product of Step 2 (38 g) was dissolved, in toluene (400 mL). To this, 2,2,2-trichloroethyl chloroformate (90 mL) was added. The reaction mixture was heated to reflux under Argon purging for 3 hr. The reaction mixture was allowed to cool to 25° C. and concentrated under vacuum to give ~200 g crude material. Purification was performed as follows on the BIOTAGE® AB ISOLERA™ flash chromatography system. Crude product (50 g) was loaded on a SNAP cartridge containing 340 g silica gel and eluted using a gradient of acetone and hexane. Fractions containing product were pooled and evaporated under vacuum. Yield of purified product (combined runs): 42 g. 1H NMR (CDCl3): 1.2 δ (3H, —CH—CH3 of isopropyl), 2.8 δ (6H, —N—(CH3)), 2.5, 2.6, 3.1 δ (1H, 1H, 1H —CH2-CH—CH3 of isopropyl), 3.8 δ (3H, —OCH3), 6.8-7.5 δ (9H, phenyl rings). Mass spectrometry: m/z=469 (M+H), 486 (M+H2O)

Step 4: 3-(3-methoxyphenyl)-1,5-dimethyl-3-phenylpyrrolidin-2-imine

The product of Step 3 (40 g) was dissolved in tetrahydrofuran (500 mL). The solution was cooled to 0° C. using ice bath and stirred under Argon for 30 min. Then, 60 g zinc dust followed by 60 mL of formic acid (90%) was added to the reaction mixtures and stirring continued at 0° C. for 3 hr under argon purging. The stirring was continued at 25° C. for 16 hr under argon purging. Then, the reaction mixture was filtered and concentrated under vacuum. Crude Step 4 product was carried forward without purification.

Step 5: 3-(3-methoxyphenyl)-1,5-dimethyl-3-phenylpyrrolidin-2-one

Product from Step 4 (20 g) was added to 5N hydrochloric acid and the reaction mixture was refluxed under argon purging. To this mixture was added in portions 160 g of sodium nitrite dissolved in water (200 mL). The reaction mixture was refluxed for 30 min further and cooled to 25° C. and extracted with chloroform (2000 mL). The organic layer was dried on anhydrous sodium sulfate, was filtered and then was concentrated under vacuum to obtain dark brown colored crude product of Step 5 (12 g). The crude product was purified on the BIOTAGE® AB ISOLERA™ flash chromatography system as follows: The crude product was dissolved in chloroform (10 mL) and was loaded on a SNAP cartridge containing 340 g silica gel. The column was eluted with a gradient of ethyl acetate and hexane. Fractions containing product were pooled and evaporated under vacuum to obtain viscous yellow oil (21 g). 1H NMR (CDCl3): 1.2 δ (3H, —CH—CH3 of isopropyl), 2.8 δ (3H, —N—(CH3)), 2.2, 3.1, 3.5 δ (1H, 1H, 1H —CH2-CH—CH3 of isopropyl), 3.8 δ (3H, —OCH3), 6.8-7.5 δ (9H, phenyl rings). Mass spectrometry: m/z=296 (M+H).

Step 6: 3-(3-hydroxyphenyl)-1,5-dimethyl-3-phenylpyrrolidin-2-one

Product of Step 5 (5 g) was dissolved in dichloromethane (250 mL) and stirred at −60° C. under argon purging using dry ice and acetone. After 30 min at −60° C. and under argon purging, 1M boron tribromide in dichloromethane (45 mL) was added in drop wise manner. The reaction mixture was stirred for 3 hr at −60° C. under argon purging. Then, the reaction mixture was allowed to warm to 25° C. and stirred under argon for 2 hr at 25° C. The reaction was quenched with slow addition of methanol (50 mL) at 4° C. The reaction mixture was concentrated under vacuum and poured in cold 1N HCl (300 mL). The white precipitate was extracted with dichloromethane (500 mL). The organic layer was dried on anhydrous magnesium sulfate, was filtered and was concentrated under vacuum. The crude product was used without further purification.

Step 7: 3-(3-(tert-butyldimethylsilyloxy)phenyl)-1,5-dimethyl-3-phenylpyrrolidin-2-one Product of Step 6 (4.9 g) was dissolved in dichloromethane (200 mL). To this, imidazole (5 g) and tertiarybutyldimethylsilyl chloride (5 g) was added. The reaction mixture was stirred at 25° C. for 16 hrs. Then, the reaction mixture was extracted with water (200 mL) and the organic layer was dried on anhydrous magnesium sulfate. The organic layer was filtered and concentrated under vacuum. The crude product was loaded on a SNAP cartridge containing 340 g silica gel and eluted with a gradient of ethyl acetate and hexane using the BIOTAGE® AB ISOLERA™ flash chromatography system. Fractions containing product were pooled and evaporated to obtain product of Step 7 as a viscous, colorless oil. Yield of purified product: 2.75 g. 1H NMR (CDCl3): 0.1 δ (6H, —Si—(CH3)2), 0.9 δ (9H, (—CH3)3 of tertiary butyl), 1.3 δ (3H, —CH—CH3 of isopropyl), 2.8 δ (3H, —N—(CH3)), 2.25, 3.1, 3.5 δ (1H, 1H, 1H —CH2-CH—CH3 of isopropyl), 6.8-7.5 δ (9H, phenyl rings). Mass spectrometry: m/z=396 (M+H).

Step 8: 3-(3-(tert-butyldimethylsilyloxy)phenyl)-2-ethylidene-1,5-dimethyl-3-phenylpyrrolidine Product of Step 7 (2.5 g) was dissolved in toluene (150 mL). The solution was cooled by surrounding the flask with dry ice and the contents were stirred under argon purging for 30 min. To this was added a dispersion of ethyl lithium (25 mL, 1.7 M in butyl ether). The reaction mixture was stirred in dry ice under argon purging for 1 hr and allowed to warm to 25° C. The reaction mixture was stirred for 3 hr at 25° C.

under argon purging. Then, the reaction mixture was poured in a beaker and cooled to 0° C. using an ice bath. The reaction was quenched by slow addition of water (5 mL) to the stirring toluene solution. After the evolution of gases ceased, the reaction mixture was extracted with water (three times at 50 mL each). The organic layer was diluted with ethyl acetate (500 mL) and dried over anhydrous magnesium sulfate. The organic layer was filtered and concentrated under vacuum to obtain Step 8 product as a red-brown viscous oil (3 mL). Mass spectrometry: m/z=408 (M+H). The product was carried forward without further purification.

Step 9: 3-(2-ethylidene-1,5-dimethyl-3-phenylpyrrolidin-3-yl)phenol

Step 8 product (3 mL) was dissolved in methanol (100 mL). To this, 35% conc HCl (2.75 mL) was added and the reaction mixture was stirred at 25° C. for 24 hr. Then, the reaction mixture was evaporated under vacuum to obtain an orange-red foam. The foam was dissolved in dichloromethane (200 mL) and dried over anhydrous magnesium sulfate. The organic layer was filtered and concentrated in vacuum to obtain Step 9 product as an orange-red foam (1 g). 1H NMR (CDCl3): 0.7 δ (—CH—CH3 of isopropyl), 1.7 δ (3H, =CH—CH3 of ethylidene) 3.8 δ (3H, —N—(CH3)), 2.6, 2.8, 3.1 δ (1H, 1H, 1H —CH2-CH—CH3 of isopropyl), 4.8 δ (1H, =CH—CH3 of ethylidene) 6.8-7.5 δ (9H, phenyl rings). Mass spectrometry: m/z=294 (M+H).

Step 10: tert-butyl 2-(3-(2-ethylidene-1,5-dimethyl-3-phenylpyrrolidin-3-yl)phenoxy)acetate Product of Step 9 (1 g) was dissolved in dimethylsulfoxide (60 mL). To this, powdered potassium hydroxide (1 g) and tertiarybutyl bromoacetate (2.5 mL) was added. The reaction mixture was stirred under argon for 3 hr at 25° C. The reaction mixture was diluted with ethyl acetate (800 mL) and was extracted with water (twice at 200 mL each) and saturated sodium chloride in water (200 mL). The organic layer was dried on magnesium sulfate, was filtered, and was concentrated under vacuum. Crude product was loaded on a SNAP cartridge containing 100 g silica gel and eluted with a gradient of chloroform and methanol using the BIOTAGE® AB ISOLERA™ flash chromatography system. Fractions containing product were pooled and evaporated to obtain product of Step 10 as a red oil (0.26 g). 1H NMR (CDCl3): 1.3 δ (—CH—CH3 of isopropyl), 1.5 δ (—(CH3)3 of tertiarybutyl) 2.1 δ (3H, =CH—CH3 of ethylidene) 2.9 δ (3H, —N—(CH3)), 2.8, 3.1, 3.5 δ (1H, 1H, 1H —CH2-CH—CH3 of isopropyl), 4.4 δ (1H, =CH—CH3 of ethylidene), 4.5 (2H, —O—CH2-C(O)—) 6.8-7.5 δ (9H, phenyl rings). Mass spectrometry: m/z=408 (M+H).

Step 11: 2-(3-(2-ethylidene-1,5-dimethyl-3-phenylpyrrolidin-3-yl)phenoxy)acetic Acid Step 10 product (0.26 g) was dissolved in dichloromethane (10 mL). To this, trifluoroacetic acid (5 mL) was added and the reaction mixture was stirred at 25° C. for 1 hr. Then, the reaction mixture was evaporated under vacuum to obtain product of Step 11 (0.22 g) which was used without further purification. Mass spectrometry: m/z=352 (M+H).

Step 12: tert-butyl 2-(2-(3-(2-ethylidene-1,5-dimethyl-3-phenylpyrrolidin-3-yl)phenoxy)acetamido)ethylcarbamate Product of Step 11 (0.11 g) was dissolved in acetonitrile (10 mL). To this, N-boc-ethylene diamine (0.1 g), HBTU (0.4 g), HOBT (0.15 g), and DIPEA (1 mL) were added. The reaction mixture was stirred at 25° C. for 1 hr and was evaporated under vacuum. Residue was dissolved in dichloromethane (300 mL) and was extracted with water (twice at 200 mL each). The organic layer was dried on anhydrous magnesium sulfate and was filtered and was evaporated. Crude product was loaded on a SNAP cartridge containing 100 g silica gel and eluted with a gradient of chloroform and methanol using the BIOTAGE® AB ISOLERA™ flash chromatography system. Fractions containing product were pooled and evaporated under vacuum to obtain Step 12 (0.13 g). 1H NMR (CDCl3): 1.25 δ (—CH—CH3 of isopropyl), 1.5 δ (9H, —(CH3)3 of N-boc) 1.8 δ (3H, =CH—CH3 of ethylidene) 2.9 δ (3H, —N—(CH3)), 2.2, 2.3, 3.1 δ (1H, 1H, 1H —CH2-CH—CH3 of isopropyl), 3.3, 3.5 δ (2H, 2H, —N—CH2-CH2-N—), 4.4 δ (1H, =CH—CH3 of ethylidene), 4.5 (2H, —O—CH2-C(O)—), 6.8-7.5 δ (9H, phenyl rings). Mass spectrometry: m/z=494 (M+H).

Step 13: N-(2-aminoethyl)-2-(3-(2-ethylidene-1,5-dimethyl-3-phenylpyrrolidin-3-yl)phenoxy)acetamide 2,2,2-trifluoroacetate Product of Step 12 (0.13 g) was dissolved in dichloromethane (10 mL). To this, trifluoroacetic acid (2.5 mL) was added and the reaction mixture was stirred at 25° C. for 1 hr. The reaction mixture was evaporated under vacuum to obtain Step 13 product (0.1 g), which was carried forward without further purification.

Step 14: 2-bromo-N-(2-(2-(3-(2-ethylidene-1,5-dimethyl-3-phenylpyrrolidin-3-yl)phenoxy)acetamido)ethyl)acetamide Step 13 product (0.1 g) was dissolved in dichloromethane (50 mL). To this, DIPEA (3 mL) followed by NHS ester of bromoacetic acid (0.2 g) was added. The reaction mixture was stirred at 25° C. for 1 hr under argon and was evaporated under vacuum. Crude product was loaded on a SNAP cartridge containing 100 g silica gel and eluted with a gradient of chloroform and methanol using the BIOTAGE® AB ISOLERA™ flash chromatography system. Fractions containing product were pooled and evaporated to obtain product of Step 14 (0.1 g). 1H NMR (CDCl3): 1.3 δ (—CH—CH3 of isopropyl), 2.0 δ (3H, =CH—CH3 of ethylidene) 2.9 δ (3H, —N—(CH3)), 2.2, 2.8, 3.1 δ (1H, 1H, 1H —CH2-CH—CH3 of isopropyl), 3.5, 3.8 δ (2H, 2H, —N—CH2-CH2-N—), 4.5 δ (1H, =CH—CH3 of ethylidene), 4.4 (2H, —O—CH2-C(O)—), 4.7 δ (2H, —CH2-Br), 6.8-7.5 δ (9H, phenyl rings). Mass spectrometry: m/z=514, 516 (M+H), 530, 532 (M+H2O).

G6PDH-Product of Step 14 Conjugate

3K G6PDH (920 mg) (prepared in accordance with the procedure described in U.S. Pat. No. 6,033,890) was dissolved in 50 mM phosphate buffer containing 1 mM EDTA and 0.025 mM DTT) pH 7.2 (3 mL). To this, 0.5 M DTT (0.15 mL) was added and the reaction mixture was stirred at 4° C. for 16 hr. Activated 3K G6PDH was concentrated using AMICON® centrifugal filter tubes of 30 kDa molecular weight cut off (Millipore Corporation, Billerica Mass.). The product above was dissolved again in 50 mM phosphate buffer (containing 1 mM EDTA and 0.025 mM DTT) pH 7.2 (4 mL). To this reaction mixture was added product of Step 14 (9 mg, dissolved in 0.2 mL DMF) and the reaction mixture was stirred at 4° C. for 16 hr. 3K G6PDH-product of Step 14 conjugate was purified by diafiltration two times as described above. Yield after final purification: 9.6 mg.

MALDITOF spectrometry: G6PDH m/z=54,415. G6PDH-Step 14 m/z=54,793 (1EDDP label per enzyme monomer)

G6PDH-Product of Step 14-SH-Step 14

2.4 mg G6PDH-product of Step 14 conjugate was dissolved in 1 mL 50 mM phosphate buffer containing 1 mM EDTA, pH 7.2. To this, 0.4 mL freshly prepared iminothiolane solution (3 mg/mL) was added. Reaction mixture was incubated at 25° C. for 30 min with gentle shaking. Thiolated enzyme (G6PDH-Step 14-SH) was concentrated using AMICON® micron centrifugal filter tubes of 30 kDa molecular weight cut off. The thiolated enzyme was dissolved again in 50 mM phosphate buffer (containing 1 mM EDTA and 0.025 mM DTT) pH 7.2 (4 mL). To this solution was added product of Step 14 (9 mg, dissolved in 0.2 mL DMF) and the reaction mixture was stirred at 4° C. for 16 hr. G6PDH-product of Step 14-SH-Step 14 conjugate was purified by diafiltration two times as described. MALDITOF spectrometry: G6PDH-Step 14 m/z=54,793, G6PDH-Step 14-SH-Step 14 m/z=57,130 (4.4 EDDP labels per enzyme monomer).

Assay for EDDP Analyte

The experiments were conducted on an AGILENT® 8453 UV spectrophotometer (Agilent Technologies, Santa Clara Calif.). Typically, 2.5 mL Tris buffer (50 mM, containing 3.3 mM $MgCl_2$, pH 7.8), 0.2 ml anti-EDDP antibody (1 mg/mL, commercially available from Lin Zhi International Inc. Sunnyvale Calif.), 0.1 mL glucose-6-phosphate (0.1 M), 0.1 mL NADP (0.006M) were taken in a quartz cuvette. To this, 0-4029 ng/mL EDDP in 10 μL methanol was added and mixed well. Then, 10 μL G6PDH-product of Step 14-SH-Step 14 (1 mg/mL) was added and mixed well. Increase in the absorbance at 340 nm was monitored at 1 min after the enzyme addition. The results are summarized in Table 1 below.

TABLE 1

| EDDP (ng/mL) | mAu 340 nm |
|---|---|
| 0 | 432 |
| 370 | 456 |
| 1221 | 497 |
| 4029 | 561 |

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. An antibody complex comprising (i) an antibody specific for 2-ethylidene-1,5-dimethyl-3,3-diphenylpyrrolidine complexed to (ii) a conjugate having a label linked to 2-ethylidene-1,5-dimethyl-3,3-diphenylpyrrolidine at the 3-position of one of the phenyl rings by means of the terminal oxygen atom of the linking group

—$(CH_2)C(O)NH(CH_2)(CH_2)NHC(O)(CH_2)O$—.

2. The antibody complex according to claim 1 wherein the label moiety is selected from the group consisting of enzymes, polynucleotides coding for a catalyst, promoters, dyes, fluorescent molecules, chemiluminescent molecules, coenzymes, enzyme substrates, radioactive groups, small organic molecules, amplifiable polynucleotide sequences and particles.

3. The antibody complex according to claim 1 wherein the label moiety is an enzyme.

* * * * *